(12) United States Patent
Gramnas

(10) Patent No.: US 8,784,501 B2
(45) Date of Patent: Jul. 22, 2014

(54) OSSEOINTEGRATED LIMB PROSTHESIS

(75) Inventor: Finn Gramnas, Kinna (SE)

(73) Assignee: Ossur HF, Reykjavic (IS)

( * ) Notice: Subject to any disclaimer, the term of this patent is extended or adjusted under 35 U.S.C. 154(b) by 1226 days.

(21) Appl. No.: 11/962,693

(22) Filed: Dec. 21, 2007

(65) Prior Publication Data

US 2008/0161938 A1    Jul. 3, 2008

Related U.S. Application Data

(63) Continuation of application No. PCT/SE2006/000656, filed on Jun. 5, 2006.

(30) Foreign Application Priority Data

Jun. 28, 2005 (SE) .................................. 0501501

(51) Int. Cl.
*A61F 2/74* (2006.01)
(52) U.S. Cl.
USPC ............................................................ 623/27
(58) Field of Classification Search
USPC ..................... 623/13.12, 16.11, 27
See application file for complete search history.

(56) References Cited

U.S. PATENT DOCUMENTS

| | | | |
|---|---|---|---|
| 3,947,897 A | 4/1976 | Owens | |
| 5,895,429 A * | 4/1999 | Cool et al. | ....................... 623/27 |
| 6,425,925 B1 | 7/2002 | Grundei | |
| 6,482,238 B1 * | 11/2002 | Grundei | ......................... 623/32 |
| 6,626,951 B1 | 9/2003 | Gramnaes | |
| 6,709,466 B1 | 3/2004 | Grundei | |

FOREIGN PATENT DOCUMENTS

DE    10040617    3/2002

OTHER PUBLICATIONS

Supplementary European Search Report issued in connection with corresponding EP Application No. 06747850.

* cited by examiner

*Primary Examiner* — Thomas J Sweet
*Assistant Examiner* — Matthew Schall
(74) *Attorney, Agent, or Firm* — Gesmer Updegrove LLP

(57) ABSTRACT

A limb prosthesis which via coupling means is adapted to be connected to an implant in the form of an osseointegrated shaft projecting from an amputated stump. The coupling means comprises a flexible joint and the prosthesis further comprises at least one force transmitting device secured to and extending from a prosthetic member connected to the coupling means up to a position on the amputated stump or body portion to which the stump connects. The force transmitting device is adapted to be secured to the stump or other body portion in such a way that it relieves the implant from at least part of the bending and/or rotational forces exerted to the prosthetic member.

10 Claims, 9 Drawing Sheets

OSSEOINTEGRATED LIMB PROSTHESIS

PRIORITY INFORMATION

The present application is a continuation of International application Serial No. PCT/SE2006/000656, filed Jun. 5, 2006 that claims priority to Swedish Application Serial No. SE 0501501-1, filed on Jun. 28, 2005. Both applications are incorporated by reference on their entireties.

TECHNICAL FIELD

The present invention refers to a limb prosthesis which via coupling means is adapted to be connected to an implant in the form of an osseointegrated shaft projecting from an amputated stump

BACKGROUND OF THE INVENTION

Traditional prostheses, leg prostheses as well as arm prostheses, use a socket for connecting the prosthesis to the body. The socket is applied onto the remaining part of the user's limb, the so called "stump". This means that the transmission of forces between the prosthesis and the user takes place via the remaining soft tissues on the stump. Especially for leg prostheses, which have to carry the body weight of the user, this results in a non-desired so called pumping effect, which means that the soft tissues on the stump inserted into the socket will be pressed together when loaded and be extended when unloaded. In other words there will be an undesired relative movement between the soft tissues and the bones of the user's stump.

This pumping effect causes wear and damage of the tissues. It further results in instability, which may cause a risk for stumbling and leads to a compensating gait with hip-hiking. The gait is more energy consuming and causes stress on the hip, foot and back. It further leads to a low perception for motion and position of the prosthesis.

Socket connection however has several advantages, such as that it permits a high activity level and the risk for fatigue of the material in the prosthesis is low. In order to function well socket connection requires that the stump is relatively long, at which the length of the stump is calculated from the closest joint, which for a below knee amputated is the knee joint and for an above knee amputated is the hip joint. For an arm amputated the length of the stump is in a corresponding way calculated from the elbow joint or the shoulder joint respectively.

It is also previously known to connect a prosthesis to an implant, i.e. an osseointegrated shaft or screw of titanium. The forces between the user and the prosthesis takes place directly from the skeleton system to the prosthesis, and not via the soft tissues of the user. This means that the "pumping effect" is eliminated as well as the problems related thereto such as tissue damages and instable gait. It further gives a good perception of motion and position of the prosthesis. The energy consumption will be lower due to the absence of motion between skeleton and soft tissue. Osseointegrated prostheses may further be used on amputation levels where traditional socket applications are not working properly, mainly amputations with very short stumps, such as high above knee amputations, close below knee joint amputations and close to elbow joint and close to shoulder joint amputations.

The disadvantages are that the rehabilitation period is lengthy since it takes a long time to obtain the necessary strength in the implant in order to be able to put a load on it and an even longer time to reach the maximum activity level. Maximum activity level is still limited and the wearer is for example not recommended to run. A high activity level involves a risk for damage on the part of the implant penetrating the skin, the so called abutment, the bone to which the implant is attached or the metal components adjoining to the implant. Since damage of the bone tissue has to be avoided the dimensions of the implant are normally made weak enough so that when overloaded the abutment will break first. The implant normally has a good strength in axial direction, i.e. when exerted to compressive and pulling forces. It however has a much lower strength when exerted to torsional and bending moments. This is the reason why the freedom of movement for an osseointegrated leg prosthesis is limited and that the user is for example not recommended to run.

DE-A1-100 40 617 discloses an osseointegrated leg prosthesis wherein at least one of the prosthesis components is provided with a material weakening which when a certain load is exceeded will break before the implant or the bone tissue breaks.

U.S. Pat. No. 5,888,215 discloses a lower leg prosthesis wherein the leg stump is relieved from vertical forces acting on it from the socket by means of a mechanism that transfers forces from the prosthesis directly to the tibia. This mechanism comprises an implant extending transversely into the tibia and which is connectable to the socket.

U.S. Pat. No. 6,482,238 discloses an upper leg stump prosthesis connected to a shaft implanted in a truncated femur. An open mesh netting structure covers a portion of the proximal shaft and allows bone tissue to grow into it. A cone-shaped adaptor is provided at the distal end of the shaft and permits the attachment of a substitute for a condyle.

U.S. Pat. No. 3,947,897 discloses an osseointegrated prosthesis, which comprises a circular pressure pad carried adjacent the upper end of the prosthesis for engaging the flesh of the stump. This pressure pad may take up tensile and pressure forces but is not adapted to take up any bending or rotational forces.

U.S. Pat. No. 5,895,429 discloses a leg prosthesis with lockable knee joint, wherein a locking element is provided for locking respectively releasing the prosthesis parts relative to each other. This prosthesis is not osseointegrated.

OBJECT AND MOST IMPORTANT FEATURES OF THE INVENTION

An object of the present invention is to provide an limb prosthesis having most of the advantages of osseointegrated prostheses but which reduces transfer of bending and/or rotational forces to the implant, which will enable a higher loading of the prosthesis, especially in the form of bending and/or rotational forces, and thus will enable a higher maximum activity level for the prosthesis wearer. These and further objects have according to the invention been achieved by a limb prosthesis which via coupling means is adapted to be connected to an implant in the form of an osseointegrated shaft projecting from an amputated stump, said coupling means comprises a flexible joint and said prosthesis further comprises a force transmitting device secured to and extending from a prosthetic member connected to the coupling means up to a position on the amputated stump or body portion to which the stump connects. The force transmitting device is adapted to be secured to the stump or other body portion in such a way that it relieves the implant from at least part of the bending and/or rotational forces exerted to the prosthetic member.

According to one embodiment said force transmitting device comprises a socket adapted to accommodate the stump, said socket having one end portion secured to the prosthetic member and an opposite end portion secured around at least a substantial part of the circumference of the stump.

In one aspect of the invention the two end portions of the socket are interconnected by at least one rigid arm member.

In a further aspect of the invention said coupling means is adapted to permit tilting of said prosthetic member with respect to the implant in one, more or all directions.

In still a further aspect of the invention the coupling means is adapted to permit rotation of said prosthetic member with respect to the implant.

According to one embodiment said coupling means comprises a first coupling member fixedly connected with the implant and a second coupling member fixedly connected with the prosthetic member, wherein one of said coupling members comprises a ball member having a spherical or part-spherical surface and the other coupling member comprises a housing adapted to receive said ball member and to permit tilting of said ball member in the housing.

According to a further embodiment the coupling means comprises a first coupling member fixedly connected with the implant and a second coupling member fixedly connected with the prosthetic member, wherein one of said coupling members comprises a rotatable member having a spherical, part-spherical or cylindrical surface and the other coupling member comprises a housing adapted to receive said rotatable member and to permit rotation of said rotatable member in the housing.

In one aspect of the invention the coupling means is adapted to prevent tilting movement of the implant with respect to the prosthetic member connected thereto.

In a further aspect of the invention the said coupling means is adapted to prevent relative rotational movement of the implant with respect to the prosthetic member connected thereto.

In a still further aspect of the invention the coupling means is adapted to prevent relative axial movement of the implant with respect to the prosthetic member connected thereto.

According to one embodiment a locking member is provided for locking the first coupling member in axial direction with respect to the second coupling member, said locking member being operated by an operating member from the outside of the coupling means and is by said operating member adjustable in two positions, a locking position in which it prevents relative axial movement of the first and second coupling members and a releasing position in which it permits the first and second coupling members to be released from each other.

In a further embodiment one of said coupling members comprises a ball member having a spherical or part-spherical surface and the other coupling member comprises a housing adapted to receive said ball member and that said locking member extends through the wall of the housing and has an engagement member at its end projecting into the housing, said engagement member having a part-spherical inner contact surface being adapted to engage with the ball member and further has a recess in said part-spherical contact surface, the locking member with its engagement member being rotatable with respect to the housing by means of the operating member, wherein in one rotated position—locking position—the engagement member prevents axial movement of the ball member with respect to the housing, and in another rotated position—releasing position—the recess of the engagement member is located such that it allows the ball member to be released from the housing.

BRIEF DESCRIPTION OF DRAWINGS

The invention will be described in the following in greater detail by way of examples and with reference to the accompanying drawings, in which:

FIG. 4 b is a corresponding cut but displaced 90° with respect to the section in FIG. 4 a.

DESCRIPTION OF PREFERRED EMBODIMENTS

Figure 1:
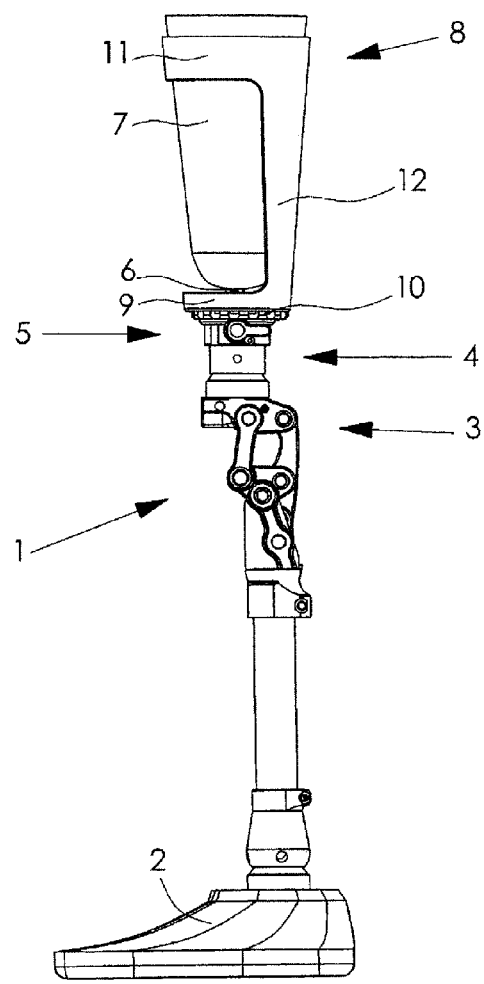
FIG. 1 is a side view of an above knee amputation with a prosthesis according to the invention.

FIG. 1 shows an above knee amputation comprising a leg prosthesis 1, comprising a prosthetic foot 2, a prosthetic knee 3 and various adjustable connecting couplings. The prosthetic knee shown in the drawings is of a type disclosed in U.S. Pat. No. 6,808,540 and will not be further described. A prosthetic member 4, which according to FIG. 1 constitutes a part of the upper leg prosthesis is via coupling means 5 connected to an implant 6 in the form of an osseointegrated shaft, for example a titanium screw. The implant 6 is integrated into the skeleton of an amputated stump 7.

The stump 7 is held in a socket 8, which in a manner described more in detail below will relieve the implant 6 from at least part of the bending and/or rotational forces exerted to the prosthetic member 4. Such forces will instead be transferred via the socket 8, which acts as a force transmitting device. The socket 8 has one end portion 9 secured to a connector sleeve 10 of the prosthetic member 4 and an opposite end portion 11 tightened around the stump 7. At least one arm 12 extends between the two end portions of the socket 8. The arm(-s) 12 preferably extends along the sides, along the front or along the back side of the stump 7 as shown in FIGS. 1 and 2.

Figure 6:
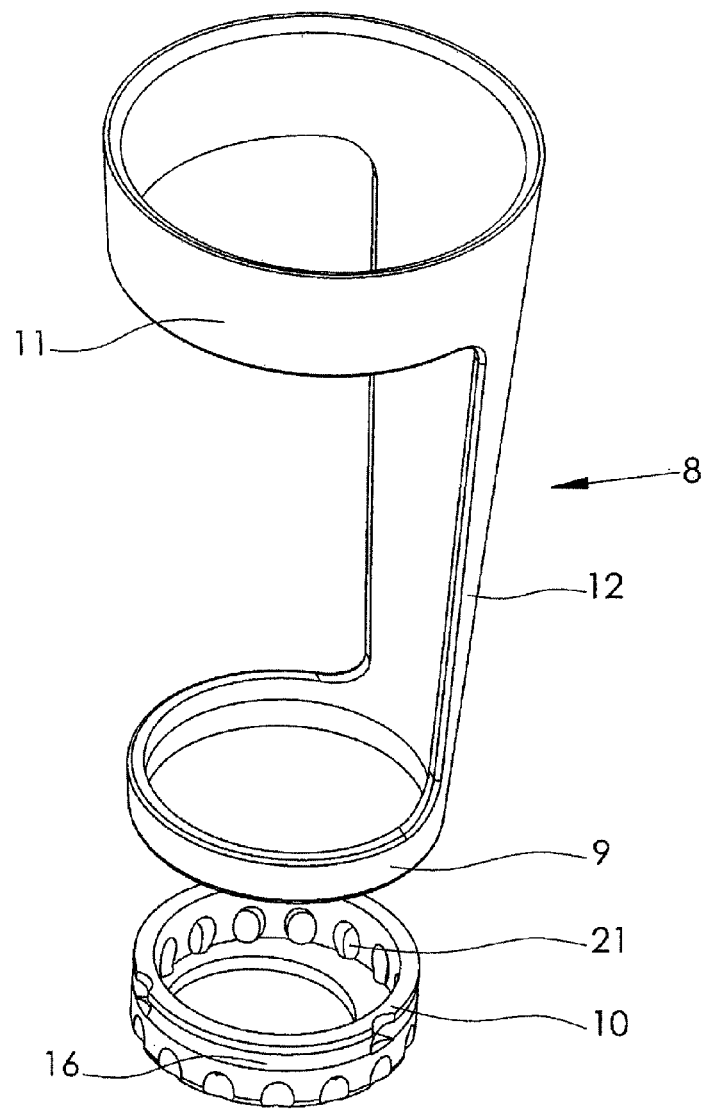
FIG. 6 is a perspective view of the socket constituting the force transmitting device and a connector sleeve connecting the socket to the housing of the coupling means.

The connector sleeve 10 and the socket 8 are shown in more detail in FIG. 6. The socket 8 is laminated to the connector sleeve 10, which has a circumferential groove 16. The connector sleeve 10 is further provided with a plurality of holes 21 which provides a good ventilation of the area of the stump 7 surrounding the implant 6. A poor ventilation of this area may cause tissue damages.

The coupling means 5 is a flexible joint, which means that is adapted to permit tilting of the implant 6 with respect to the prosthetic member 4 in one, more or all directions. Alternatively or in addition to tilting it may permit rotation of the implant 6 with respect to the prosthetic member 4.

Figure 2:
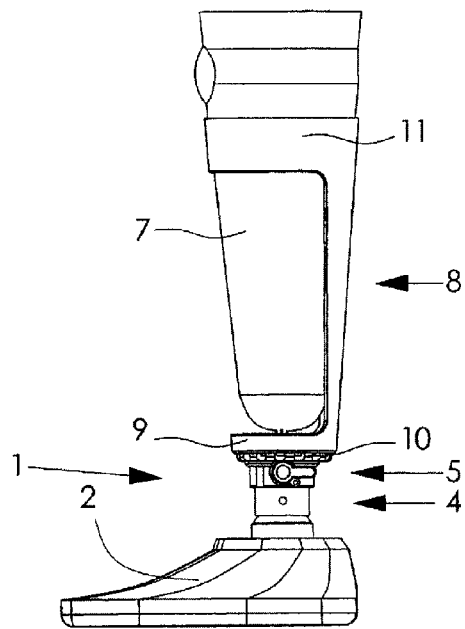
FIG. 2 is a side view of a below knee amputation with a prosthesis according to the invention.

FIG. 2 shows a below knee amputation wherein the prosthetic member 4, which is attached to the coupling means 5, forms a part of the lower leg prosthesis. The device is in other respects similar to the one described in connection with FIG. 1.

The coupling means 5 is as mentioned above a flexible joint, so that the implant 6 will be relieved from at least a substantial part of the bending and/or rotational forces exerted to the prosthetic member 4. In the embodiment shown in the drawings the coupling means 5 comprises a first coupling member in the form of a ball member 13, having a part-spherical outer surface, said ball member is provided at the free end of the implant 6 projecting from the stump 7.

The prosthetic member 4 is attached to a second coupling member 14 of the coupling means 5, said second coupling member 14 is adapted to be connected to the first coupling member, ball member 13, of the implant 6. The second coupling member 14 comprises a housing having a part-spherical inner surface 15 adapted to receive the ball member 13 and to lock it in axial direction in the housing 14. The housing 14 is forming a part of the prosthetic member 4.

In the embodiment shown in the drawings relative rotational movement between the two coupling members 13 and 14 is prevented by an axial groove 17 provided in the part-spherical outer surface of the ball member 13 and engaging with a shoulder 18 on the inner surface 15 of the housing 14. However for some applications, such as for prostheses intended to be worn during the rehabilitation period when the implant has not reached its full strength, the implant may not be allowed to take up any rotational forces, at which rotational movement of the implant 6 with respect to the prosthetic member 4 should be permitted.

It may further for certain applications be desirable that only rotational movement of the implant 6 with respect to the prosthetic member should be allowed, while tilting should be prevented. In such case the ball member 13 may be replaced by a cylindrical member and the housing 14 be adapted to receive the cylindrical member so that it can rotate therein at least to a limited extent.

Figure 4A:
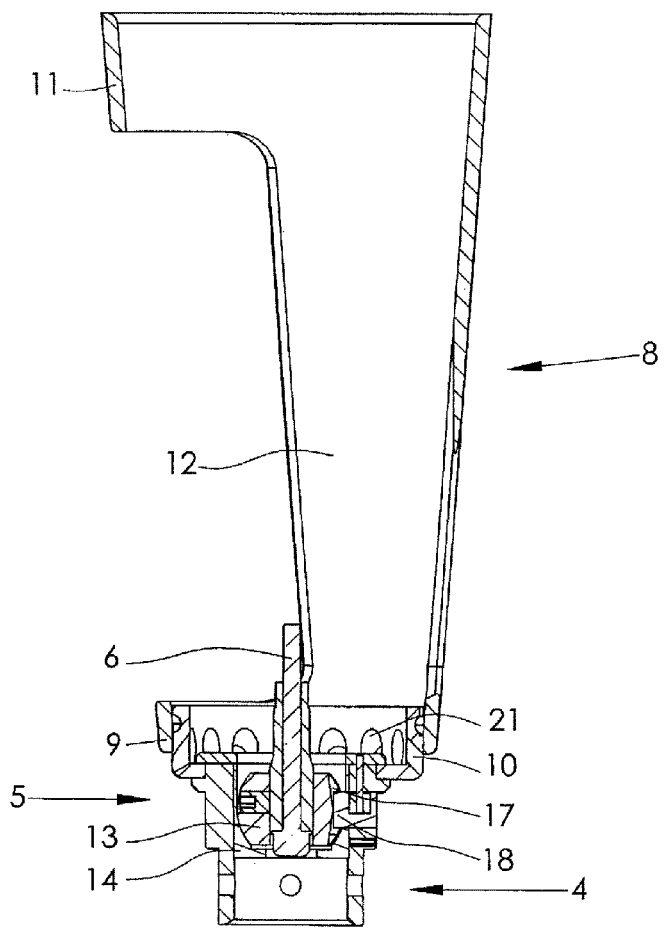
FIG. 4 a is a longitudinal cut through a prosthetic member, coupling means with an implant connected thereto, and a socket constituting a moment arm.
Figure 4B:
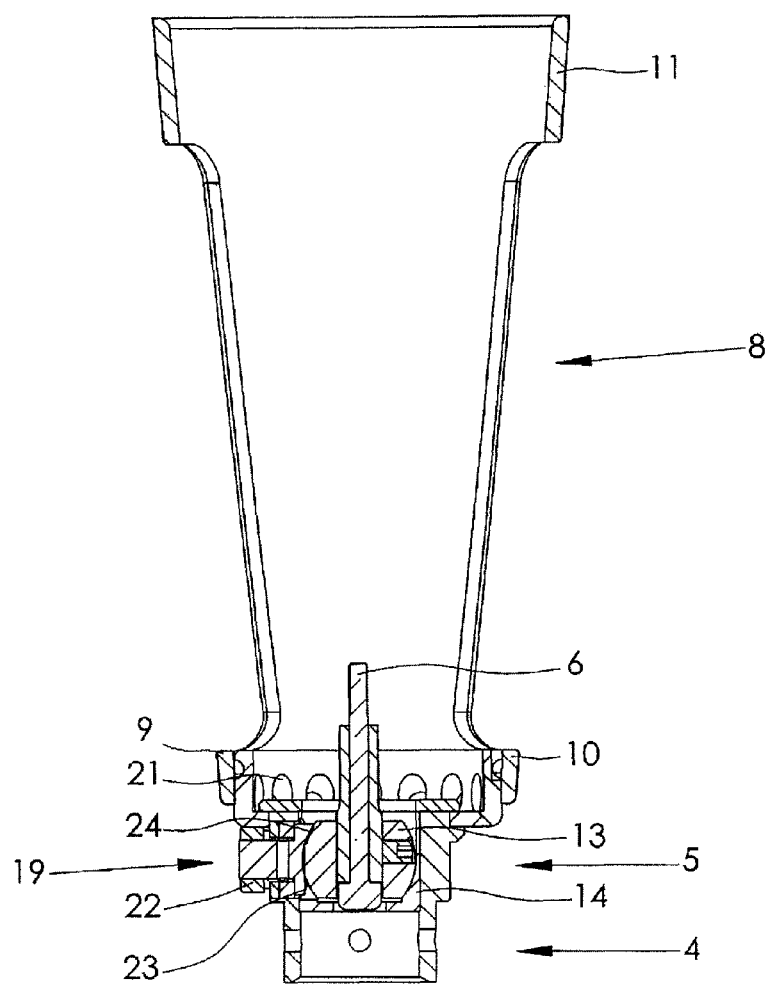
Figure 5:
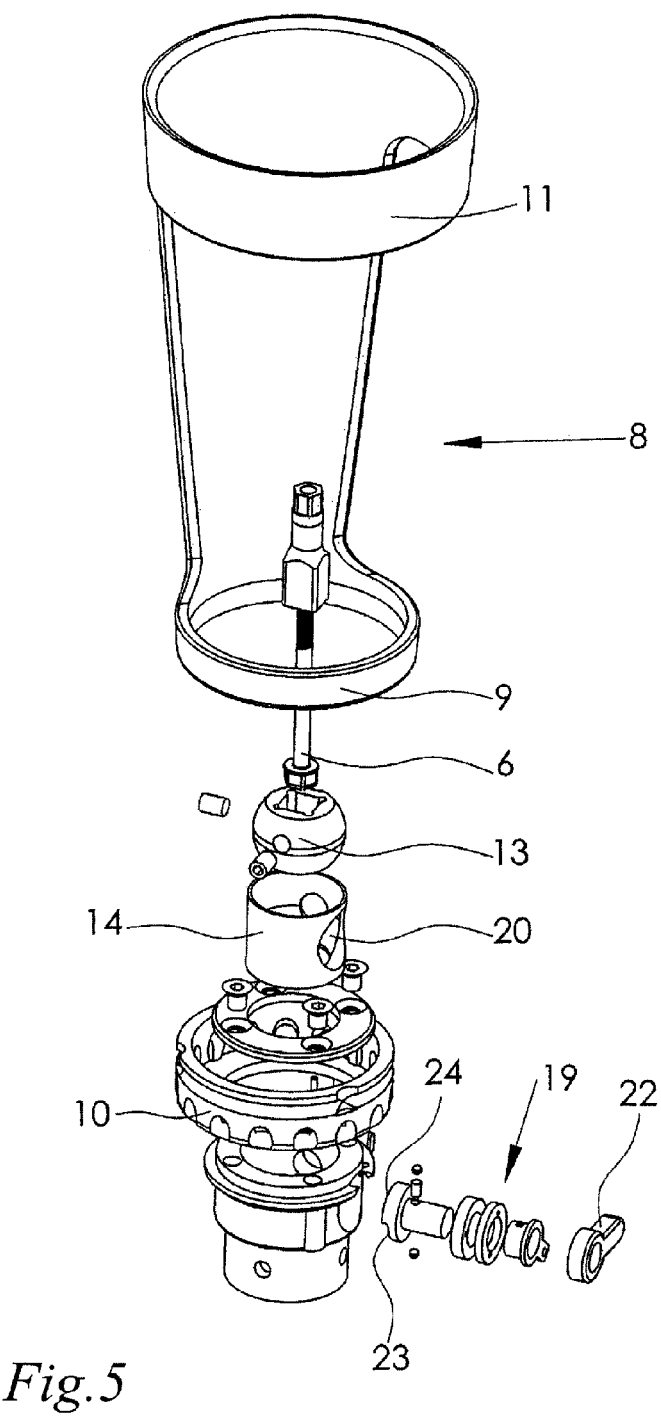
FIG. 5 is an exploded view of the device shown in FIGS. 4 a and b.
Figure 7:
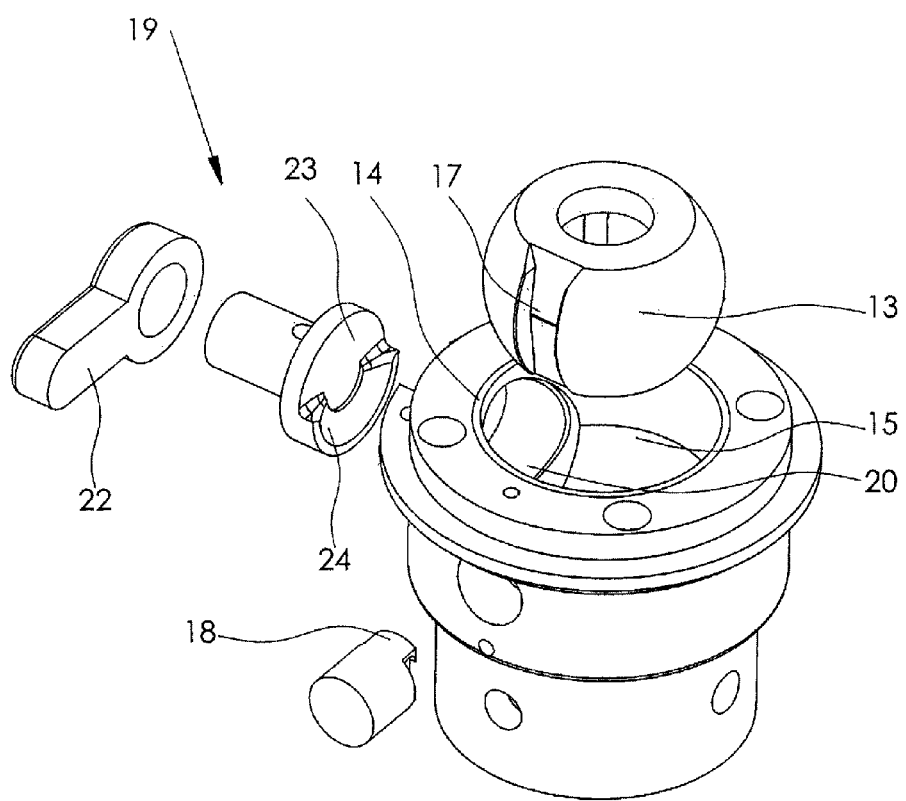
FIG. 7 is a perspective view of the coupling means.

Locking of the ball member 13 in axial direction in the housing 14 is provided by a locking member 19 extending in radial direction through a hole 20 in the housing 14. The locking member 19 is rotatably mounted in the housing 14 and is operated by a lever 22 on the outside of the housing 14. The end surface of the locking member 19 extending into the housing 14 has a recessed portion 23 and a curved locking surface 24 adapted to engage with a part of the spherical surface of the ball member 13 to prevent it from being withdrawn from the housing 14 when located in its upper position as shown in FIG. 4b. When the locking member 19 by means of the lever 22 is rotated 180° the curved locking surface 24 will be turned downwards and the recessed portion 23 upwards, as shown in FIG. 7, in which position the ball member 13 may pass into or out of the housing 14.

At least a part of the bending forces exerted on the prosthesis during different kinds of activities such as walking and running will be transferred to the socket 8 acting as a force transmitting device and the load is distributed over the end portion 11 which encloses the leg at a position located at a distance above the implant 6. This distance is preferably as large as possible. In the case of a high above knee amputation it may be necessary to apply the end portion 11 of the socket 8 around the waist of the wearer. The flexible joint, i.e. the coupling device 5 comprising the ball member 13 and the housing 14, which permits tilting of the implant 6 with respect to the prosthetic member 4 when exerted to bending forces, enables the implant 6 to be relieved from at least part of these bending forces.

As mentioned above the flexible joint may be designed in other ways than described above. For some applications, such as for prostheses intended to be worn during the rehabilitation period when the implant has not reached its full strength, the implant 6 may not be allowed to take up any rotational forces. In this case rotational movement of the implant 6 with respect to the prosthetic member 4 should be permitted, so that at least a part of both rotational and bending forces are transferred to the socket 8. It may also be possible to have a coupling device which may only rotate, and not tilt, wherein only rotational forces are transferred to the socket.

Figure 3A:
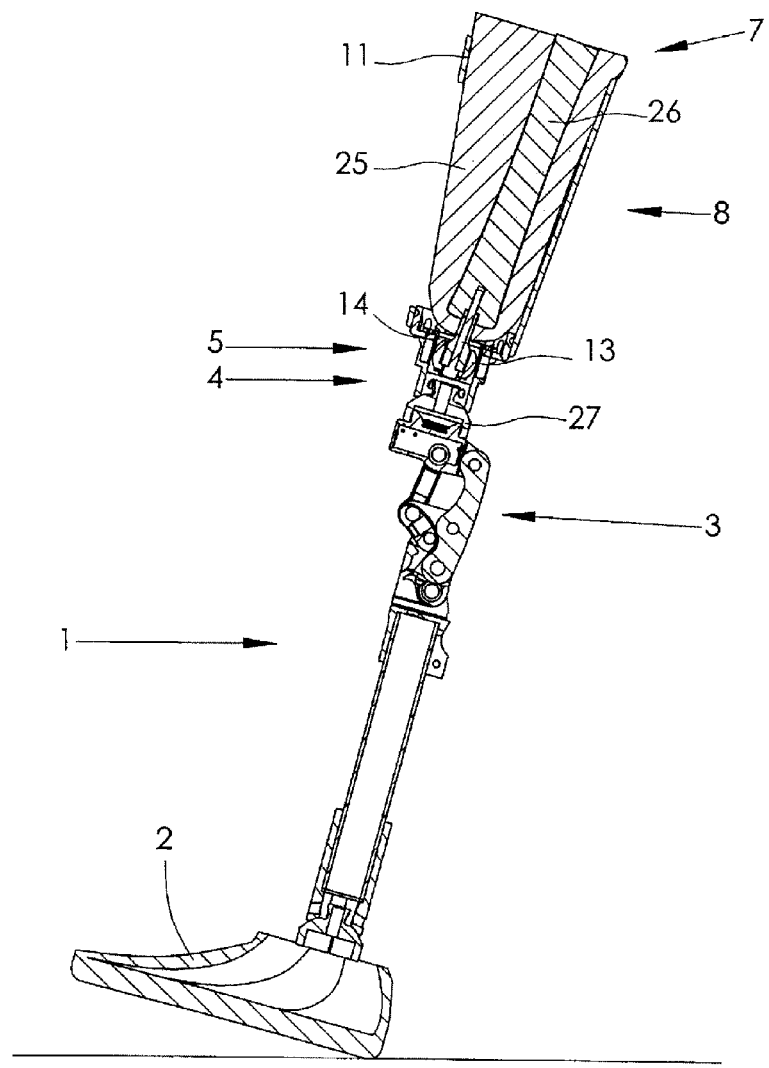
FIG. 3 a-c are longitudinal cuts through the stump of an above knee amputation with a prosthesis according to the invention shown in different positions of a walking cycle.
Figure 3B:
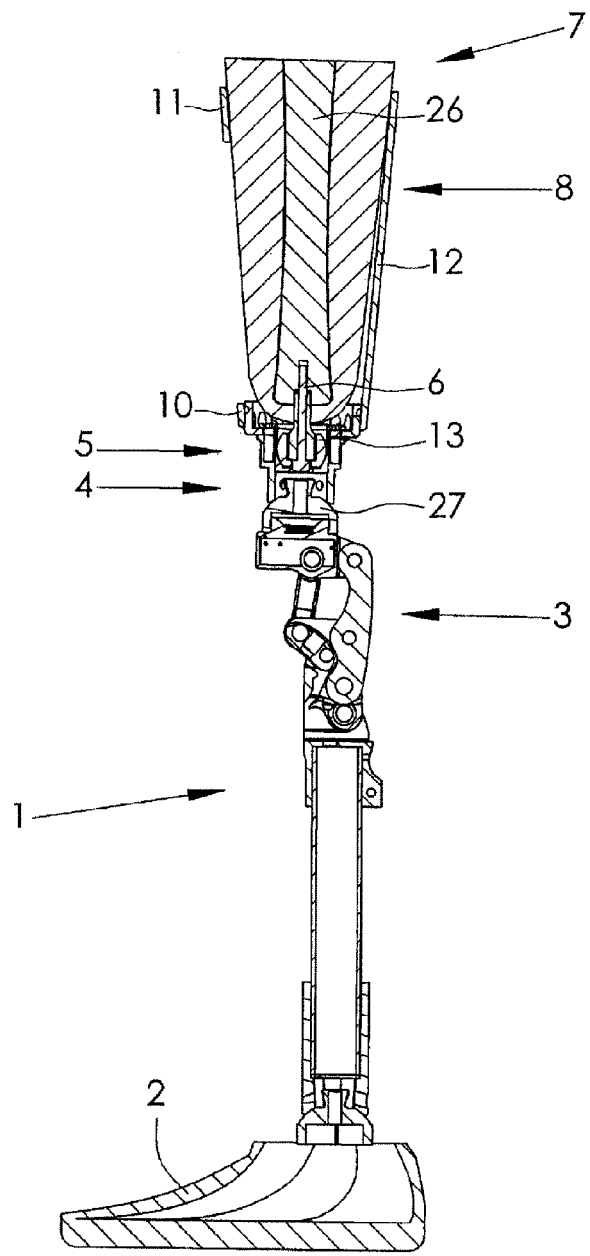
Figure 3C:
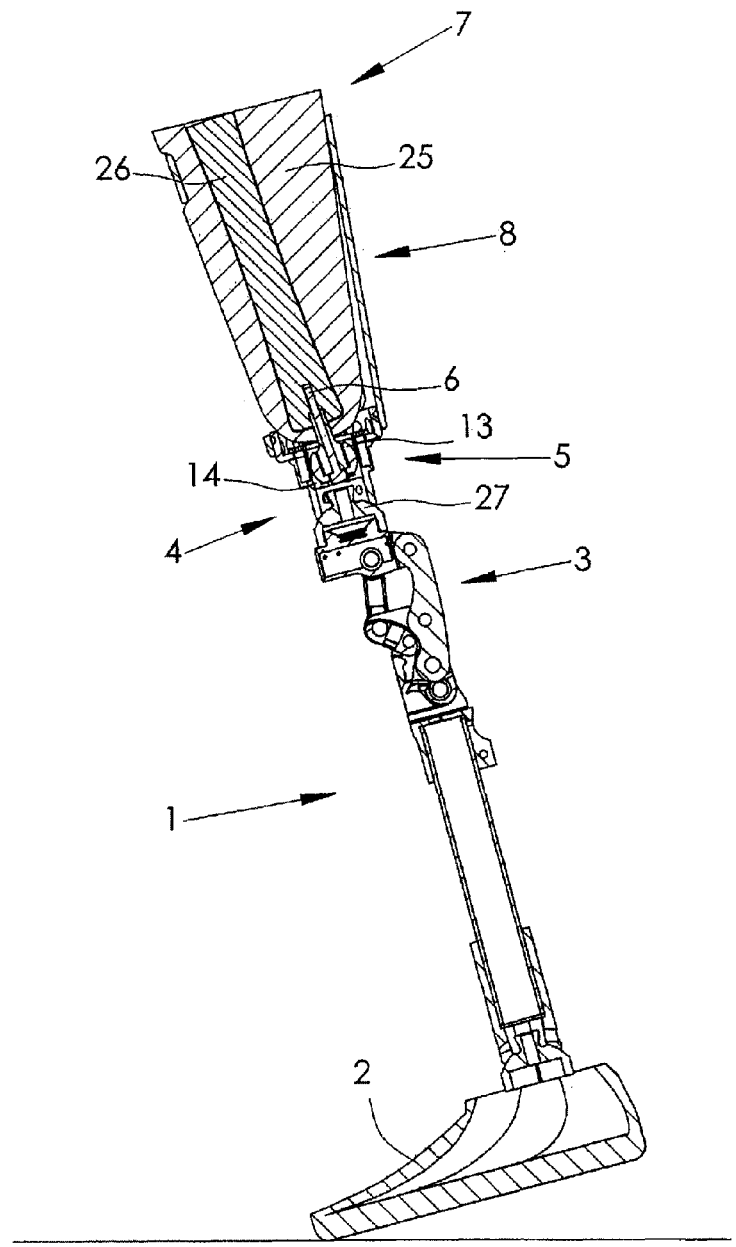

The part of the bending and/or rotational forces that are transferred from the prosthetic member 4 to the socket 8 will be distributed over the ring-shaped end portion 11 which encloses the leg and will be taken up as a compression or deformation of the soft tissues 25 of the wearer. This is illustrated in FIGS. 3 a-c, wherein FIG. 3 a shows the initial phase, heel strike, of the walking cycle in which the heel strikes the ground and the wearer starts to put load on the leg. The skeleton member 26, to which the implant 6 is secured, is permitted to move with respect to the soft tissues 25 surrounding it and with respect to the prosthetic member 4, to relieve the implant from bending forces. Bending forces from the prosthetic member 4 transferred to the socket will compress the soft tissues 25 between the socket 8 and the skeleton member 26 on the rear side of the stump 7.

FIG. 3 b shows the mid stance position when the whole foot rests against the ground and the body weight acts essentially right through the leg in parallel therewith. No substantial bending forces are transferred to the socket 8.

FIG. 3 c shows the toe off phase when supporting oneself on the toe while extending the leg to initiate the swing phase with the leg swinging freely in the air. A part of the body weight rests in this position still upon the leg. Just as in the heel strike position the skeleton member 26, to which the implant 6 is secured, is permitted to move with respect to the soft tissues 25 surrounding it and with respect to the prosthetic member 4, to relieve the implant form bending forces. Bending forces from the prosthetic member 4 transferred to the socket 8 will compress the soft tissues 25 between the socket 8 and the skeleton member 25 on the front side of the stump 7.

The similar happens when rotational forces are transferred from the prosthetic member 4 to the socket 8. The skeleton member 26, to which the implant 6 is secured, is permitted to move (rotate) with respect to the soft tissues 25 surrounding it and with respect to the prosthetic member 4, to relieve the implant form rotational forces.

The prosthetic member 4 may comprise additional components, such as a torque limiting coupling having an adjustable resistance against rotation and/or tilting and which when for example the rotational force exerted thereto exceeds the selected value will rotate a certain angle, for example 90°. Such torque limiting couplings are well-known in prosthetic technique and will therefore not be described in greater detail. Thus the torque limiting coupling will take up rotational forces and/or bending forces exceeding a selected value, while forces up to the selected value are taken up by the implant 4 and according to the invention by the implant and/or the socket 8.

As is shown in FIG. 3 a-c the prosthetic knee 3 is connected to the upper leg prosthesis via angularly adjustable connection means in the form of a frustopyramidal socket 27, which per se is known from for example U.S. Pat. No. 3,659,294 and will therefore not be described in detail herein.

The new coupling device according to the invention between the implant 6 and the prosthesis combines the advantages of the traditional socket application and osseointegration, while it avoids many of the drawbacks related to these techniques. Since a considerable part of the bending and/or rotational forces are not transferred to the implant, but are instead taken up by the socket 8, the implant 6 is relieved from such loads. In this way the prosthesis can be loaded with greater forces without risking that the prosthesis, the implant or the skeleton member to which the implant is secured, breaks. The rehabilitation period may be shortened since the implant may be loaded earlier. It will further enable a higher maximum activity level for the prosthesis user and may allow the user to run and to use the prosthesis in other situations where it is exerted to bending and/or rotational forces.

It is important to note that the force transmitting device in the form of socket 8 can not be compared with a traditional socket, since it does not have to carry the body weight of the user and therefore all the disadvantages of traditional socket application in the form of pumping effect causing wear and damage of the tissues are avoided.

It is understood that the invention has been described with reference to one embodiment thereof, while several modifications are possible within the scope of the claims. Thus the coupling means for connecting the implant to the prosthesis may be varied as long as it permits tilting and/or rotation between the implant and the prosthesis.

The socket 8 acting to take up at least a part of bending and/or rotational forces can be replaced by other means, such as a belt or band tightened around the stump and connected to a rigid bar (corresponding to arm 12) which is secured to the prosthetic member.

Although having been described only with reference to a leg prosthesis the device according to the invention may as well be applied to an arm prosthesis.

The invention therefore intends to cover any variations or equivalents which are within known or customary practice within the technical field to which it belongs.

The invention claimed is:

1. A limb prosthesis which via coupling means is adapted to be connected to an implant in the form of an osseointegrated shaft projecting from an amputated stump, wherein a prosthetic member defines an upper terminal end of said limb prosthesis, wherein said coupling means comprises a flexible joint adapted to permit tilting of said implant with respect to the prosthetic member in one, more, or all directions, wherein a force transmitting device is secured to and extends from the prosthetic member up to a position on the amputated stump or body portion to which the stump connects, said force transmitting device comprises a socket adapted to accommodate the stump, said socket having one end portion secured to the prosthetic member and an opposite end portion secured around at least a substantial part of the circumference of the stump or other body portion, wherein the two end portions of the socket are interconnected by at least one rigid arm member, and wherein the implant is allowed to tilt with respect to the socket and to the prosthetic member so that the implant is relieved from at least part of the bending forces exerted to the prosthetic member.

2. A limb prosthesis as claimed in claim 1, wherein said coupling means is adapted to permit rotation of said implant with respect to the prosthetic member.

3. A limb prosthesis as claimed in claim 1 wherein said coupling means comprises a first coupling member fixedly connected with the implant and a second coupling member fixedly connected with the prosthetic member, wherein one of said coupling members comprises a ball member having a spherical or part-spherical surface and the other coupling member comprises a housing adapted to receive said ball member and to permit tilting of said ball member in the housing.

4. A limb prosthesis as claimed in claim 1 wherein said coupling means comprises a first coupling member fixedly connected with the implant and a second coupling member fixedly connected with the prosthetic member, wherein one of said coupling members comprises a rotatable member having a spherical, part-spherical or cylindrical surface and the other coupling member comprises a housing adapted to receive said rotatable member and to permit rotation of said rotatable member in the housing.

5. A limb prosthesis as claimed in claim 1, wherein said coupling means prevents relative rotational movement of the implant with respect to the prosthetic member connected thereto.

6. A limb prosthesis as claimed in claim 1, wherein said coupling means prevents relative axial movement of the implant with respect to the prosthetic member connected thereto.

7. A limb prosthesis as claimed in claim 6, wherein a locking member is provided for locking the first coupling member in axial direction with respect to the second coupling member, said locking member being operated by an operating member from the outside of the coupling means and is by said operating member adjustable in two positions, a locking position in which it prevents relative axial movement of the first and second coupling members and a releasing position in which it permits the first and second coupling members to be released from each other.

8. A limb prosthesis as claimed in claim 7, wherein one of said coupling means comprises a ball member having a spherical or part-spherical surface and the other coupling member comprises a housing adapted to receive said ball member and that said locking member extends through an opening in the wall of the housing and has an engagement member at its end projecting into the housing, said engagement member having a part-spherical inner contact surface being adapted to engage with the ball member and further has a recess in said part-spherical contact surface, the locking member with its engagement member being rotatable with respect to the housing by means of the operating member, wherein in one rotated position—locking position—the engagement member prevents axial movement of the ball member with respect to the housing, and in another rotated position—releasing position—the recess of the engagement member is located such that it allows the ball member to be released from the housing.

9. A limb prosthesis having a prosthetic member leading to a prosthetic joint, said prosthetic member being connected by a coupling means to an implant in the form of an osseointegrated shaft projecting from an amputated stump, said coupling means comprising a first coupling member secured to a free end of said osseointegrated shaft, and a second coupling member secured to said prosthetic member, said first and second coupling members being interengaged and movable with respect to each other in a manner permitting said implant to tilt with respect to said prosthetic member in one, more or all directions, and a force transmitting device secured to and extending from said prosthetic member up to a position on the amputated stump or body portion to which the stump connects, said force transmitting device comprising a socket adapted to accommodate the stump, said socket having one end portion secured to said prosthetic member and an opposite end portion secured around at least a substantial part of the stump or other body portion, wherein the two end portions of the socket are interconnected by at least one rigid arm member, and wherein said implant is allowed to tilt with respect to the socket and to the prosthetic member.

10. A limb prosthesis adapted to be connected to an amputated stump having an implant in the form of an osseointegrated shaft projecting therefrom, said limb prosthesis comprising:
- a prosthetic member defining a terminal upper end of said limb prosthesis;
- a force transmitting device secured to and extending from said prosthetic member up to a position on the amputated stump or body portion to which the stump connects, said force transmitting device comprising a socket adapted to accommodate the stump, said socket having one end fixed to said prosthetic member and an opposite end secured around at least a substantial part of the stump or other body portion, with at least one rigid arm member connecting the two ends of said socket; and
- coupling means for connecting said osseointegrated shaft to said prosthetic member, said coupling means comprising a first coupling member secured to a free end of said osseointegrated shaft and a second coupling member secured to said prosthetic member, said first and second coupling members being interengaged and movable with respect to each other in a manner permitting said osseointegrated shaft to tilt with respect to said prosthetic member and said force transmitting device in one, more or all directions.

* * * * *